United States Patent
Krongauz et al.

(10) Patent No.: US 6,627,121 B1
(45) Date of Patent: Sep. 30, 2003

(54) PHOTOCHROMIC NAPHTHOPYRAN COMPOUNDS

(75) Inventors: Valeri Krongauz, Rehovot (IL); Emmanuel Lurie, Lod (IL); Alexandre Chif, Rostov-on-Don (RU); Judith Ratner, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 10/048,888

(22) PCT Filed: Aug. 3, 2000

(86) PCT No.: PCT/IL00/00463

§ 371 (c)(1),
(2), (4) Date: Jun. 10, 2002

(87) PCT Pub. No.: WO01/10858

PCT Pub. Date: Feb. 15, 2001

(51) Int. Cl.$^7$ ............ G02B 5/23; C07D 311/92; C07D 413/10

(52) U.S. Cl. ............ 252/586; 528/196; 528/198; 528/199; 524/110; 544/150; 549/389

(58) Field of Search ............ 544/150; 549/389; 252/586; 528/198

(56) References Cited

FOREIGN PATENT DOCUMENTS

| WO | WO 99/31081 A1 | 6/1999 |
|---|---|---|
| WO | WO 01/10858 A1 | 2/2001 |

*Primary Examiner*—Robert W. Ramsuer
(74) *Attorney, Agent, or Firm*—Browdy and Neimark

(57) ABSTRACT

A photochromic naphthopyran of formula (I) wherein $R_1$ through $R_{15}$, which may be the same or different, are independently selected from the group consisting of hydrogen, $C_1$–$C_4$ alkyl, $C_1$–$C_4$ alkoxy, halogen, $C_1$–$C_4$ alkylcarbonyloxy, benzoyloxy, $C_3$–$C_6$ cycloalkyl, phenyl, and $NR_{16}R_{17}$, wherein $R_{16}$ and $R_{17}$ are each $C_1$–$C_4$ alkyl or together with the N atom form a 5–12 membered monocyclic or polycyclic ring having, optionally, one or more further heteroatoms; R is hydrogen, alkyl or alkoxy; and $>C(C_nH_{2n=1})(C_mH_{2m=1})$ is a tert-alkylene grup, wherein n and m are integers from 1 to 5.

11 Claims, No Drawings

PHOTOCHROMIC NAPHTHOPYRAN COMPOUNDS

FIELD OF THE INVENTION

The present invention relates to certain novel photochromic naphthopyran compounds and to compositions and articles comprising them.

BACKGROUND OF THE INVENTION

Naphthopyran compounds are known to be capable of exhibiting a photochromic effect and have been found to be useful for imparting photochromic properties to a polymeric host material. Naphthopyrans and their use in photochromic lenses have been described for example, in U.S. Pat. No. 4,826,977. U.S. Pat. No. 5,066,818, U.S. Pat. No. 5,238,981, U.S. Pat. No. 5,520,853, U.S. Pat. No. 5,552,090, U.S. Pat. No. 552,091, U.S. Pat. No. 5,623,005, U.S. Pat. No. 5,658, 501, U.S. Pat. No. 5,932,725, EP 401958 and WO 95/05371, and have been reviewed by Crano et al., *Pure & Appl. Chem.* 68 (1996) pp.1395–1398, and by Van Gemert et al., *Mol. Cryst. Liq. Cryst.* 297 (1997) pp.131–138.

Photochromic naphthopyrans give yellow to blue colors. In combination with other naphthopyrans or with other photochromes such as spirooxazines, they give neutral gray or brown colors. Incorporation of these compounds into a plastic lens or another plastic article provides the articles with desirable photochromic properties. High photoinduced optical density, together with a high speed of thermal decoloration in the dark, are among the most desirable combination of properties that provide eyes with good protection, from intensive sunlight and fast lens color clearing in areas shaded from the sun.

The present invention relates to novel photochromic naphthopyran compounds containing a phenyl alkyl substituent in the naphthalene moiety of the photochrome that have enhanced optical density of the photoinduced color and fast decoloration speed in the dark. None of the publications mentioned above describe the compounds of the present invention.

SUMMARY OF THE INVENTION

In accordance with the present invention, a photochromic naphthopyran compound of the formula I is provided:

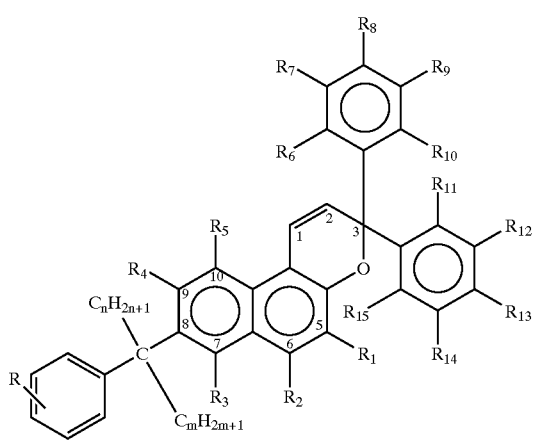

(I)

wherein $R_1$ through $R_{15}$, which may be the same or different, are independently selected from the group consisting of hydrogen, $C_1$–$C_4$ alkyl, $C_1$–$C_4$ alkoxy, halogen, $C_1$–$C_4$ alkylcarbonyloxy, benzoyloxy, $C_3$–$C_6$ cycloalkyl, phenyl, and $NR_{16}R_{17}$, wherein $R_{16}$ and $R_{17}$ are each $C_1$–$C_4$ alkyl or together with the N atom form a 5–12 membered monocyclic or polycyclic ring having, optionally, one or more further heteroatoms;

R is hydrogen, $C_1$–$C_4$ alkyl or $C_1$–$C_4$ alkoxy, and $(C_nH_{2n+1})$—C—$(C_mH_{2m+1})$ is a tert-alkylene group, wherein n and m are integers from 1 to 5.

The alkyl and alkoxy radicals according to the invention may be linear or branched and have 1–4, preferably 1–2, more preferably, 1 carbon atom, e.g. methyl and methoxy radicals. $R_1$ through $R_{15}$ may be halogen selected from chloro, bromo, iodo and, preferably, fluoro. When $NR_{16}R_{17}$ denotes a ring, it may be a saturated, unsaturated or aromatic 5–12 membered mono—or polycyclic ring having optionally one or more heteroatoms selected from nitrogen, oxygen or sulfur, such as, for example, but not being limited to, pyrrolidine, pyrroline, piperidine, pyridine, piperazine, pyrimidine, quinoline, morpholine, thiazoline, thiazole, oxazoline, oxazole, and the like, and is preferably a saturated 5–6 membered, more preferably a 6-membered, ring optionally containing an oxygen atom, e.g. piperidino and morpholino.

The present invention further provides synthetic methods for making the photochromic naphthopyran molecules of formula I.

The naphthopyran compounds of the present invention be used as additives to polymers employed on optical filters of variable optical density, including plastic lenses to provide light-sensitive darkening effects.

DETAILED DESCRIPTION OF THE INVENTION

The present invention provides photochromic naphthopyran compounds of formula I.

The photochromic naphthopyran of formula I may be prepared by reacting the appropriately substituted benzophenone with sodium acetylide in a suitable solvent. The substituted propargyl alcohol obtained in this reaction is then coupled by a modified Claisen rearrangement with the appropriately substituted 2-naphthol in the presence of a suitable acid catalyst under mild reaction conditions to give the desired naphthopyran of formula I.

The starting benzophenone may be prepared by Friedel-Crafts reaction in which the benzoylchloride derivative is reacted with a substituted benzene derivative. The substituted 2-naphthol is formed by alkylation of a molecule of β-naphthol by α-methylstyrene.

In the naphthopyran compounds of formula I, R and $R_1$ through $R_5$ are preferably hydrogen; $R_6$ through $R_{15}$ are preferably hydrogen, methoxy, methyl, fluor, dimethylamino, piperidino or morpholino; n and m are preferably 1 such that the group >C($C_nH_{2n+1}$)($C_mH_{2m+1}$) is preferably tert-propylene ($C(CH_3)_2$). These functionalities can be synthesized by chemical reactions known in the art, once one understands the present invention.

The photochromic naphthopyrans of the invention, alone or together with other photochromic substances, may be incorporated into a polymeric host material such as, but not being limited to, polycarbonate, polyurethane, polyacrylate, polymethacrylate, polystyrene or a copolymer of polyacrylate or polymethacrylate with polystyrene.

The aforementioned photochromic compounds of the invention or its mixtures can also be incorporated into organic plastic articles such as, for example, optical lenses, e.g. ophthalmic and piano lenses, visors, car windshields or other articles, giving high optical density of color on irradiation with sunlight. The incorporation of the photochromic compounds can be carried out by any conventional method known in the art, for example, by molding techniques, e.g., injection-moulding, press-moulding or by polymerization techniques, e.g., by thermal polymerization of a photochrome solution in a polymerizable monomer containing a catalyst, for example, azo-isobutyronytryl, giving free radicals on heating. Microencapsulation techniques can also be employed. A photochromic compound may be incorporated in a polymer host also by thermodiffusion through the lens surface. In one embodiment, a mixture of different photochromes can be incorporated into a plastic object.

The blends of the photochromes of the invention with polymers and polymer compositions provide high quality photochromic plastic objects, especially plastic lenses with high optical density on photoactivation, high fatigue resistance and fast decoloration in the dark.

Thus, in another embodiment, the present invention further relates to a photochromic plastic -organic article, preferably a plastic lens, comprising a plastic object containing the aforementioned photochrome with a photochrome known in the art and/or comprising other ingredients such as plasticizers, light stabilizers and materials for the photochrome micro-encapsulation.

The invention will now be illustrated by the following examples, to which it is not limited.

EXAMPLES

Example 1

Preparation of 3-(4-Methoxyphenyl)-3-(2-fluorophenyl)-8-(2-phenylisopropyl)-3H-naphtho[2,1b]pyran.

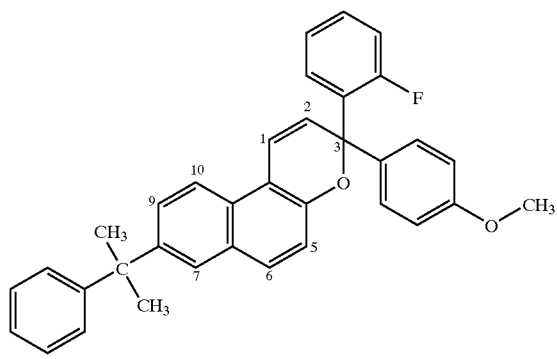

(2)

1a. 6-Phenylisopropyl-2-hydroxy naphthalene. A solution of 110 ml (1 mol) of α-methylstyrene in 150 ml of dichloromethane was added dropwise to a solution of 124g (0.86 mol) of β-naphthol and 20 ml of methanesulfonic acid in 750 ml of o-dichlorobenzene. The reaction mixture was kept at room temperature by cooling with cold water and stirring. After 3 hrs, the mixture was rinsed with water and a solution of NaHCO₃. The organic layer was separated, dried and evaporated. The residue was fractionated by vacuum distillation and sublimation, giving after crystallization from petroleum ether, the product with a yield of 65%.

1b. 3-(4-Methoxyphenyl-3-(2fluorophenyl-8-(2-phenylisopropyl3H-naphtho-[2,1b]pyran. A mixture of 21g (0.08 mol) of 6-phenylisopropyl-2-hydroxy naphthalene, 20.5 g (0.08 mol) of 3-(4-methoxyphenyl)-3-(2fluorophenyl)-3-hydroxy-propine, prepared as described in the art (see, for example, Van Gemert et al. U.S. Pat. No. 5,066,818) and a catalytic amount of 4-toluenesulfonic acid monohydrate dissolved in benzene was stirred for 5 hrs at room temperature. The solvent was evaported and the material obtained was crystallized from petroleum ether. Yield, 50%. $\lambda_{max}$ of the photo activated form is 462 nm.

Examples 2–6

The compounds listed below as Examples 2–6 were prepared by a synthetic procedure analogous to that described in Example 1.

Example 2

3,3-Di(4-Methoxyphenyl)-8-(2-phenylisopropyl)-3H-naphtho [2,1b]pyran; $\lambda_{max}$=500 nm.

Example 3

3,3Di(4-Dimethylaminophenyl)-8-(2-phenylisopropyl)-3H-naphtho[2,1b]-pyran; $\lambda_{max}$= 560 nm.

Example 4

3 -(2-Fluorophenyl)3(4-piperidinophenyl)-8-(2-phenylisopropyl)-3H-naphtho[2,1b]pyran; $\lambda_{max}$=528 nm.

Example 5

3-(2-Fluorophenyl)-3-(4-dimethylaminophenyl)-8-(2-phenylisopropyl)-3H-naphtho[2,1b]pyran; $\lambda_{max}$= 540nm.

Example 6

3-(2-Fluorophenyl)-3-(4-morpholinophenyl)-8-(2-phenylisopropyl)3H-naphtho[2,1b]pyran; $\lambda_{max}$=517 nm.

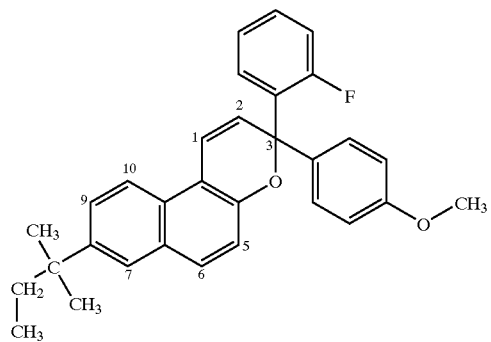

Comparative Example 7

Preparation of 3-(4-Methoxyphenyl)-3-(2-fluorophenyl)-8-tert-amyl-3H-naphtho[2,1b]pyran.

7a. 5-Tert-amyl-2-hydroxy naphthalene. A solution of 87 ml (0.8 mol) of tert-amyl alcohol in 100 ml dichloromethane was added dropwise to a mixture of 116 g (0.8 mol) of β-naphthol and 25 ml of methanesulfonic acid dissolved in 450 ml of dichlorobenzene. The reaction mixture was kept at 40° C. by cooling with cold water and stirring during 3 hrs. Further purification was performed as described in Example 1a above. Yield, 40%.

7b. 3-(4-Methoxyphenyl)-3-(2-fluorophenyl)-8-(tert-amyl-3H-naphtho[2,1b]pyran was prepared according to procedure 1b above. Yield, 50%.

Example 8

The photochromes described in Examples 1 and 7, and the compound 3-(4-methoxyphenyl)-3-(2-fluorophenyl)-3H- naphtho[2,1b]pyran, described in U.S. Pat. No. 5,066,818, denoted in Table 1 as Example 8, were individually incorporated (5%) in a polystyrene film of 5 μm. The results of the photochromic property examinations of the compounds are presented in Table 1. Here, OD is the optical density of the photochrome at the photoinduced color absorption maximum ($\lambda_{max}$), and τ½ is the halftime of color fading in the dark.

TABLE 1

| Compound Example | ($\lambda_{max}$) (nm) | OD | τ½ (min) | Color |
|---|---|---|---|---|
| 1 | 462 | 1.69 | 6.5 | Orange |
| 7 | 464 | 1.68 | >>15.0 | Yellow |
| 8 | 460 | 0.27 | 2.5 | Yellow |

Table 1 shows that substitution of the naphthalene moiety with the phenylalkyl group according to the invention (Compound 1) leads to a high photoinduced optical density and preserves sufficiently short decay times of the color and shifts the color to orange, which makes the photochrome very suitable for use in filters of tunable optical density, such as sun ophthalmic lenses or windows.

What is claimed is:

1. A photochromic naphthopyran of the formula I:

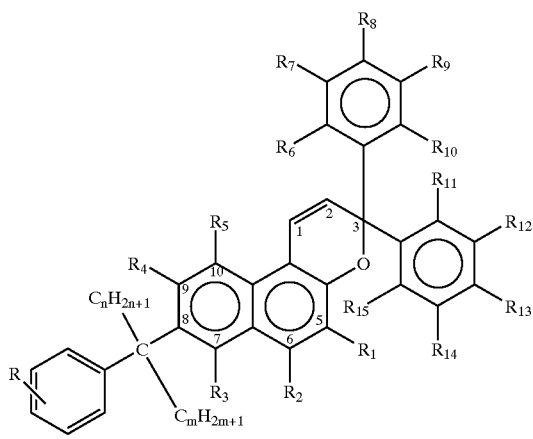

(I)

wherein $R_1$ through $R_{15}$, which may be the same or different, are independently selected from the group consisting of hydrogen $C_1$–$C_4$ alkyl $C_1$–$C_4$ alkoxy, halogen, $C_1$–$C_4$ alkylcarbonyloxy, benzoyloxy, $C_3$–$C_6$ cycloalkyl, phenyl, and $NR_{16}R_{17}$ wherein $R_{16}$ and $R_{17}$ are each $C_1$–$C_4$ alkyl or together with the N atom form a 5–12 membered monocyclic or polycyclic ring having optionally, one or more further heteroatoms;

R is hydrogen, $C_1$–$C_4$ alkyl or $C_1$–$C_4$ alkoxy, and
>C($C_nH_{2n+1}$)($C_mH_{2m+1}$) is a tert-alkylene group, wherein n and m are integers from 1 to 5.

2. The naphthopyran of claim 1 wherein R and $R_1$ through $R_5$ are hydrogen; $R_6$ though $R_{15}$ are hydrogen, methoxy, methyl, fluor, dimethylamino, piperidino or morpholino; and the group>C($C_nH_{2n+1}$)($C_mH_{2m+1}$) is —C($CH_3$)$_2$.

3. 3-(4-Methoxyphenyl)-3-(2-fluorophenyl)-8-(2phenylisopropyl)-3H-naphtho-[2,1b]pyran.

4. 3,3-Di(4-methoxyphenyl)-8-(2-phenylisopropyl)-3H-naphtho[2,1b]pyran.

5. 3,3-Di(4-dimethylaminophenyl)-8-(2-phenylisopropyl)-3H-naphtho[2,1b]pyran.

6. 3-(2-fluorophenyl)-3-(4-piperidinophenyl)-8-(2-phenylisopropyl)3H-naphtho-[2,1b]pyran.

7. 3-(2-fluorophenyl)-3-(4 -dimethylaminophenyl)-8-(2-phenylisopropyl)-3H-naphtho[2,1b]pyran.

8. 3-(2-fluorophenyl)-3-(4-morpholinophenyl)-8-(2-phenylisopropyl)-3H-naphtho[2,1b]pyran.

9. A plastic organic photochromic article comprising a plastic host material having a photochromic compound of any one of claims 1 to 8, or a mixture thereof.

10. A plastic organic photochromic article according to claim 9, further comprising other ingredients such as photochromes, plasticizers, light stabilizers and materials for the photochrome micro-encapsulation.

11. A photochromic article according to claim 9 or 10, said article being a plastic lens.

* * * * *